(12) United States Patent
Ben Muvhar (10) Patent No.: US 10,368,974 B2
(45) Date of Patent: Aug. 6, 2019

(54) GALLBLADDER IMPLANTS AND SYSTEMS AND METHODS FOR THE DELIVERY THEREOF

(71) Applicant: LithiBlock Ltd., Peduel (IL)

(72) Inventor: Shmuel Ben Muvhar, Peduel (IL)

(73) Assignee: LithiBlock Ltd., Peduel (IL)

( * ) Notice: Subject to any disclaimer, the term of this patent is extended or adjusted under 35 U.S.C. 154(b) by 140 days.

(21) Appl. No.: 15/147,080

(22) Filed: May 5, 2016

(65) Prior Publication Data
US 2016/0242796 A1    Aug. 25, 2016

Related U.S. Application Data

(63) Continuation-in-part of application No. PCT/IL2015/051051, filed on Oct. 27, 2015.
(Continued)

(51) Int. Cl.
*A61F 2/04* (2013.01)
*A61B 17/221* (2006.01)
(Continued)

(52) U.S. Cl.
CPC ............. *A61F 2/04* (2013.01); *A61B 17/221* (2013.01); *A61F 2/844* (2013.01); *A61F 2/848* (2013.01);
(Continued)

(58) Field of Classification Search
CPC . A61B 17/221; A61B 2017/2212; A61F 2/95; A61F 2/86; A61F 2/844;
(Continued)

(56) References Cited

U.S. PATENT DOCUMENTS

| 4,531,933 A | 7/1985 | Norton et al. |
| 5,643,309 A | 7/1997 | Myler et al. |

(Continued)

FOREIGN PATENT DOCUMENTS

| CN | 1863488 | 11/2006 |
| CN | 102670330 | 9/2012 |

(Continued)

OTHER PUBLICATIONS

Advisory Action Before the Filing of an Appeal Brief and Applicant-Initiated Interview Summary dated Jul. 15, 2015 From the US Patent and Trademark Office Re. U.S. Appl. No. 13/260,382.
(Continued)

*Primary Examiner* — Dinah Baria (57) ABSTRACT

A filter device for implantation in a gallbladder, including: a filtering portion configured to filter gallstones of a certain minimum size to prevent them from exiting the gallbladder through an opening of the gallbladder; a tail extending from the filtering portion away from the opening of the gallbladder and towards a distal wall of the gallbladder; and, a stopper located at a distal end of the tail, near the distal wall of the gallbladder when the filter device is implanted; wherein the filtering portion, stopper and the tail are configured to be of sufficient overall length within the gallbladder that they, when taken together, prevent migration of the filtering portion away from the opening of the gallbladder.

4 Claims, 10 Drawing Sheets

Related U.S. Application Data (60) Provisional application No. 62/069,164, filed on Oct. 27, 2014.

(51) Int. Cl.

| | | |
|---|---|---|
| *A61F 2/844* | (2013.01) | |
| *A61F 2/848* | (2013.01) | |
| *A61F 2/86* | (2013.01) | |
| *A61F 2/95* | (2013.01) | |
| *A61F 2/90* | (2013.01) | |
| *A61F 2/01* | (2006.01) | |
| *A61F 2/08* | (2006.01) | |

(52) U.S. Cl.
CPC ................. *A61F 2/86* (2013.01); *A61F 2/90* (2013.01); *A61F 2/95* (2013.01); *A61B 2017/2212* (2013.01); *A61F 2/01* (2013.01); *A61F 2002/041* (2013.01); *A61F 2002/0817* (2013.01); *A61F 2002/8486* (2013.01)

(58) Field of Classification Search
CPC .... A61F 2/848; A61F 2/04; A61F 2002/8486; A61F 2/01; A61F 2002/041; A61F 2/90; A61F 2017/2212
See application file for complete search history.

(56) References Cited

U.S. PATENT DOCUMENTS

| | | | |
|---|---|---|---|
| 5,925,062 | A | 7/1999 | Purdy |
| 6,093,199 | A | 7/2000 | Brown et al. |
| 6,342,059 | B1 | 1/2002 | Chevillon et al. |
| 6,432,134 | B1 | 8/2002 | Anson et al. |
| 6,616,680 | B1 | 9/2003 | Thielen |
| 6,623,507 | B2 | 9/2003 | Saleh |
| 7,524,319 | B2 | 4/2009 | Dubrul |
| 2002/0099437 | A1 | 7/2002 | Anson et al. |
| 2002/0193825 | A1 | 12/2002 | McGuckin, Jr. et al. |
| 2003/0040771 | A1 | 2/2003 | Hyodoh et al. |
| 2003/0057156 | A1 | 3/2003 | Peterson et al. |
| 2003/0078465 | A1 | 4/2003 | Pai et al. |
| 2003/0163204 | A1 | 8/2003 | Rix |
| 2004/0087997 | A1 | 5/2004 | Brenneman |
| 2004/0143209 | A1 | 7/2004 | Liu et al. |
| 2004/0193092 | A1 | 9/2004 | Deal |
| 2006/0036279 | A1 | 2/2006 | Eidenschink et al. |
| 2006/0074409 | A1 | 4/2006 | Schuermann |
| 2007/0027520 | A1 | 2/2007 | Sherburne |
| 2007/0083230 | A1 | 4/2007 | Javois |
| 2007/0112372 | A1 | 5/2007 | Sosnowski et al. |
| 2007/0239199 | A1 | 10/2007 | Jayaraman |
| 2008/0033457 | A1 | 2/2008 | Francischelli et al. |
| 2008/0140216 | A1 | 6/2008 | Ehrlinspiel et al. |
| 2008/0249636 | A1 | 10/2008 | Deal |
| 2008/0262592 | A1 | 10/2008 | Jordan et al. |
| 2009/0254172 | A1 | 10/2009 | Grewe |
| 2011/0230950 | A1 | 9/2011 | Knapp |
| 2012/0022550 | A1* | 1/2012 | Ben Muvhar ............. A61F 2/01 606/127 |
| 2013/0144322 | A1 | 6/2013 | Callaghan et al. |
| 2016/0317167 | A1 | 11/2016 | Ben Muvhar |
| 2017/0348086 | A1 | 12/2017 | Ben Muvhar |

FOREIGN PATENT DOCUMENTS

| | | |
|---|---|---|
| CN | 103068326 | 4/2013 |
| CN | 203424992 | 2/2014 |
| JP | 2005-508201 | 3/2005 |
| JP | 2005-534429 | 11/2005 |
| WO | WO 02/071977 | 9/2002 |
| WO | WO 2004/012587 | 2/2004 |
| WO | WO 2006/131930 | 12/2006 |
| WO | WO 2009/123715 | 10/2009 |
| WO | WO 2010/109467 | 9/2010 |
| WO | WO 2011/143137 | 11/2011 |
| WO | WO 2017/168418 | 10/2017 |
| WO | WO 2017/191645 | 11/2017 |

OTHER PUBLICATIONS

Applicant-Imitated Interview Summary dated May 27, 2015 From the US Patent and Trademark Office Re. U.S. Appl. No. 13/260,382.
Applicant-Initiated Interview Summary dated Feb. 10, 2016 From the US Patent and Trademark Office Re. U.S. Appl. No. 13/260,382.
International Preliminary Report on Patentability dated Oct. 6, 2011 From the International Bureau of WIPO Re. Application No. PCT/IL2010/000258.
International Search Report and the Written Opinion dated Feb. 3, 2016 From the International Searching Authority Re. Application No. PCT/L2015/051051.
International Search Report and the Written Opinion dated Aug. 24, 2010 From the International Searching Authority Re. Application No. PCT/IL2010/000258.
Notice of Reason for Rejection dated Nov. 29, 2013 From the Japanese Patent Office Re. Application No. 2012-501502 and Its Translation Into English.
Office Action dated Mar. 1, 2012 From the Israel Patent Office Re. Application No. 197800 and Its Translation Into English.
Official Action dated Mar. 3, 2015 From the US Patent and Trademark Office Re. U.S. Appl. No. 13/260,382.
Official Action dated Jun. 11, 2014 From the US Patent and Trademark Office Re. U.S. Appl. No. 13/260,382.
Official Action dated Sep. 11, 2013 From the US Patent and Trademark Office Re. U.S. Appl. No. 13/260,382.
Official Action dated Sep. 25, 2015 From the US Patent and Trademark Office Re. U.S. Appl. No. 13/260,382.
Official Action dated Feb. 26, 2013 From the US Patent and Trademark Office Re. U.S. Appl. No. 13/260,382.
Official Decision of Rejection dated Aug. 1, 2014 From the Japanese Patent Office Re. Application No. 2012-501502 and Its Translation Into English.
Restriction Official Action dated Dec. 6, 2012 From the US Patent and Trademark Office Re. U.S. Appl. No. 13/260,382.
Anderson et al. "7.9.1 Diameter; 7.9.4 Vessel Length", Iaizzo (Ed.), Handbook of Cardiac Anatomy, Physiology and Devices, 2nd Ed.(Chap.7): 117-118, 2010.
Elmunzer et al. "Percutaneous Cholecystostomy as a Bridge to Definitive Endoscopic Gallbaldder Stent Placement", Clinical Gastroenterology and Hepatology, 9: 18-20, 2011.
Itoi et al. "Endoscopic Gallbladder Drainage for Management of Acute Cholecystitis", Gastrointestinal Endoscopy, 71(6): 1038-1045, 2010.
Communication Pursuant to Article 94(3) EPC dated May 12, 2017 From the European Patent Office Re. Application No. 10719120.7. (4 Pages).
International Preliminary Report on Patentability dated May 11, 2017 From the International Bureau of WIPO Re. Application No. PCT/IL2015/051051. (8 Pages).
International Search Report and the Written Opinion dated Jun. 19, 2017 From the International Searching Authority Re. Application No. PCT/IL2017/050384. (14 Pages).
Invitation to Pay Additional Fees dated Aug. 17, 2017 From the International Searching Authority Re. Application No. PCT/IL2017/50499. (2 Pages).
International Search Report and the Written Opinion dated Oct. 20, 2017 From the International Searching Authority Re. Application No. PCT/IL2017/50499. (19 Pages).
Restriction Official Action dated Dec. 27, 2017 From the US Patent and Trademark Office Re. U.S. Appl. No. 15/140,505. (8 pages).
Communication Pursuant to Article 94(3) EPC dated Nov. 17, 2016 From the European Patent Office Re. Application No. 10719120.7. (6 Pages).
International Preliminary Report on Patentability dated Oct. 11, 2018 From the International Bureau of WIPO Re. Application No. PCT/IL2017/050384. (9 Pages).

(56) References Cited

OTHER PUBLICATIONS

Official Action dated May 25, 2018 From the US Patent and Trademark Office Re. U.S. Appl. No. 15/140,505. (35 Pages).
Office Action and Search Report dated Jun. 28, 2018 From the State Intellectual Property Office of the People's Republic of China Re. Application No. 201580071125.6 and Its Translation Into English.
Communication Pursuant to Article 94(3) EPC dated Feb. 4, 2019 From the European Patent Office Re. Application No. 15808269.3. (4 Pages).
Official Action dated Dec. 13, 2018 From the US Patent and Trademark Office Re. U.S. Appl. No. 15/140,505. (16 pages).
International Preliminary Report on Patentability dated Nov. 15, 2018 From the International Bureau of WIPO Re. Application No. PCT/IL2017/50499. (11 Pages).
Official Action dated Dec. 13, 2018 From the US Patent and Trademark Office Re. U.S. Appl. No. 15/140,505. (0pages).

\* cited by examiner

FIG. 10C

GALLBLADDER IMPLANTS AND SYSTEMS AND METHODS FOR THE DELIVERY THEREOF

RELATED APPLICATIONS

This application is a Continuation-in-Part (CIP) of PCT Patent Application No. PCT/IL2015/051051, filed on Oct. 27, 2015, which claims the benefit of priority under 35 USC § 119(e) of U.S. Provisional Patent Application No. 62/069,164, filed on Oct. 27, 2014.

This application is also related to U.S. patent application Ser. No. 13/260,382 filed on Sep. 26, 2011, and U.S. patent application Ser. No. 15/140,505 filed on Apr. 28, 2016.

The contents of the above applications are all incorporated by reference as if fully set forth herein in their entirety.

FIELD AND BACKGROUND OF THE INVENTION

The present invention relates generally to treating medical conditions involving ducts and/or body lumens, for example by preventing occlusion of portions of the biliary tree during treatment device deployment.

"Stones" in the gallbladder and bile ducts are found in the entire population, some of them being asymptomatic, and some—symptomatic. In the U.S., 10-15% of the adult population (more than 20 million people) suffer from bile duct stones (about 20% of the population above 65 years of age suffer from gallstones), with more than two million new cases diagnosed annually, and more than 1,800,000 cholecystectomy procedures performed annually. Patients with gallstones are classified according to three groups: symptomatic, asymptomatic and those suffering from complications caused by the gallstones, such as cholecystitis, pancreatitis or obstructive jaundice.

SUMMARY OF THE INVENTION

There is provided in accordance with an exemplary embodiment of the invention, a filter device for implantation in a gallbladder, comprising: a filtering portion configured to filter gallstones of a certain minimum size to prevent them from exiting the gallbladder through an opening of the gallbladder; a tail extending from the filtering portion away from the opening of the gallbladder and towards a distal wall of the gallbladder; and, a stopper located at a distal end of the tail, near the distal wall of the gallbladder when the filter device is implanted; wherein the filtering portion, stopper and the tail are configured to be of sufficient overall length within the gallbladder that they, when taken together, prevent migration of the filtering portion away from the opening of the gallbladder.

In an embodiment of the invention, the filtering portion, tail and stopper are configured to fit entirely and substantially uncompressed within the gallbladder.

In an embodiment of the invention, the filtering portion is comprised of spherical, circular, ovoid or oblong leaves.

In an embodiment of the invention, at least some of the leaves overlap at least partially.

In an embodiment of the invention, the stopper is split into at least two tails, each tail configured with its own stopper.

In an embodiment of the invention, the stopper is mushroom-shaped, biased towards the opening of the gallbladder.

In an embodiment of the invention, the stopper is coil-shaped.

In an embodiment of the invention, the stopper is resilient.

In an embodiment of the invention, the stopper is configured with at least two concentric circles.

In an embodiment of the invention, the filter device is comprised of a single filament.

In an embodiment of the invention, two loose ends of the single filament are attached together.

In an embodiment of the invention, the two loose ends are welded together.

In an embodiment of the invention, the filter device is configured such that the two loose ends are attached together along the tail.

In an embodiment of the invention, the device is made from at least one of a metal, a shape memory alloy and a polymer.

In an embodiment of the invention, the device is adapted for eluting a pharmaceutical after implantation.

In an embodiment of the invention, the device is at least one of bioabsorbable and biodegradable.

In an embodiment of the invention, at least one of the stopper and filtering portion are configured to prevent biofilm growth.

In an embodiment of the invention, the filtering portion is configured to filter gallstones 5 mm or greater in diameter.

In an embodiment of the invention, the stopper is configured to push gallstones of a certain minimum size away from the opening of the gall bladder.

There is further provided in accordance with an exemplary embodiment of the invention, a system for delivery of a filter device for implantation in a gallbladder, comprising: a filter device including a stopper; a guiding rod around which the filter device is at least partially wrapped; and, a catheter with an opening at a distal end, through which the guiding rod and filter device are inserted, configured for transit to the gallbladder.

In an embodiment of the invention, the filter device is wrapped on a side of the guiding rod, such that the filter device is deployable in the gallbladder without retraction of the guiding rod.

There is further provided in accordance with an exemplary embodiment of the invention, a method for implanting a filter device in a gallbladder, comprising: navigating the filter device wrapped around a guiding rod through an opening to the gallbladder for implantation, the filter device including at least a filtering portion, a tail and a stopper; withdrawing at least partially a catheter, through which the guiding rod and filter device are inserted, from the implantation site; expanding at least a portion of the filter device at least partially; and, withdrawing the guiding rod from the implantation site, leaving the expanded filter device entirely within the gallbladder and substantially uncompressed, wherein the filtering portion is disposed proximal to the opening of the gallbladder and the stopper is disposed proximal to a distal wall of the gallbladder opposite the opening after implantation.

In an embodiment of the invention, the expanding includes expanding the stopper then pushing gall stones towards the distal wall prior to expanding of the filtering portion.

In an embodiment of the invention, the pushing is performed by at least one of the guiding rod and the stopper.

In an embodiment of the invention, the filter device is implanted such that an attachment between two loose ends of the single filament filter device does not abut a wall of the gallbladder.

There is further provided in accordance with an exemplary embodiment of the invention, a filter device for implantation in a gallbladder, comprising: a filtering portion configured with a plurality of at least partly overlapping leaves to prevent gallstones of a certain minimum size from exiting the gallbladder through an opening of the gallbladder; at least one tail extending from the filtering portion away from the opening of the gallbladder and towards a distal wall of the gallbladder; and, at least one stopper located at a distal end of the at least one tail, near the distal wall of the gallbladder when the filter device is implanted; wherein the filtering portion, stopper and the tail are configured to be of sufficient overall length within the gallbladder that they, when taken together, prevent migration of the filtering portion away from the opening of the gallbladder, and, wherein the filter device is constructed of a single wire with two loose ends attached together.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example, and not necessarily to scale, and are for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

The present invention relates generally to treating medical conditions involving ducts and/or body lumens, for example by preventing occlusion of portions of the biliary tree during treatment device deployment.

Before explaining at least one embodiment of the invention in detail, it is to be understood that the invention is not necessarily limited in its application to the details of construction and the arrangement of the components and/or methods set forth in the following description and/or illustrated in the drawings. The invention is capable of other embodiments or of being practiced or carried out in various ways.

Generally, systems, devices and methods for deploying filtering devices in a gallbladder and filtering devices themselves are described. In some aspects of the invention, a blocking device and/or a blocking portion of a device are used to push gall stones away from the opening to the gallbladder in order to make space for proper deployment of a gall stone filtering device. In some embodiments of the invention, the blocking device and the filter device are components of a system. In some embodiments of the invention, the blocking device is separate from the filtering device. In some embodiments of the invention, the blocking is performed by a filtering portion of the filtering device. In some embodiments of the invention, the filtering device is two-tiered. Optionally, one tier is configured to block and/or filter. Optionally, one tier is configured to anchor the device. In some embodiments of the invention, the device is provided with a stopper, optionally on a distal end of a tail, wherein the tail, the stopper and/or the filtering/blocking section prevent substantial migration of the filter device away from an opening to the gallbladder.

In an aspect of the invention, some or all of a gallbladder filter device is constructed of a single wire or filament. In an embodiment of the invention, the single wire filter device is manufactured by placing a plurality of bends or curves in the wire (for example, forming the leaves of a filter portion and/or the curvature of a stopper). Optionally, the filter device is completed by attaching two loose ends of the wire together, for example by welding. It should be understood that an advantage of a single wire device is that there results in only one seam in the device which needs to be closed, representing an advantage in manufacturing.

It should also be understood that since seams may be more traumatic to body tissue than the rest of the device (which is probably smoother), the fewer the number of seams the better from a patient health and/or device utilization standpoint. In some embodiments of the invention, the junction between the two loose ends, which are attached to each other, occurs along a portion of the filter device that will not abut body tissue. In an embodiment of the invention, the filter device is implanted in the patient such that the seam is not proximal to, or does not abut, body tissue.

In some aspects of the invention, the devices described herein spare the patient from suffering and/or surgery, and are intended to prevent the complications of cholecystectomy and anesthesia, operative mortality, postoperative infections (wound infection and other infections), and/or delayed impacts of gallbladder absence (impaired absorption, abdominal pain, etc.) by relieving and/or preventing the symptoms of cholecystitis, pancreatitis or obstructive jaundice, and/or preventing and/or delaying the need for cholecystectomy in patients with gallstones. In some embodiments of the invention, temporary relief, for example of pain induced by gallstones, is provided.

It should be understood that exemplary filter devices described herein are intended to prevent gallstones from passing from the gallbladder into the cystic duct while still allowing for normal bile flow and/or bodily fluids and/or secretions through the biliary tree and into the duodenum. In some exemplary embodiments of the invention, filtering is achieved without exerting potentially harmful levels of expansive radial force on the walls of the cystic duct and/or gallbladder. In some embodiments of the invention, no radial force is applied on the walls of the cystic duct and/or gallbladder.

Throughout the description, "proximal" or "proximally" means in the direction closest to outside of the patient's body and "distal" or "distally" means in the opposite direction, that is in the direction further into the patient's body.

FIGS. 1A-1E are side views of a schematic deployment sequence of a blocking device 100, in accordance with an exemplary embodiment of the invention. For efficiency, description of device embodiments of the invention (FIGS. 1A-1E and FIGS. 2A-2C) are described in conjunction with the methods of their deployment, in conjunction with FIG. 7.

Figure 7:
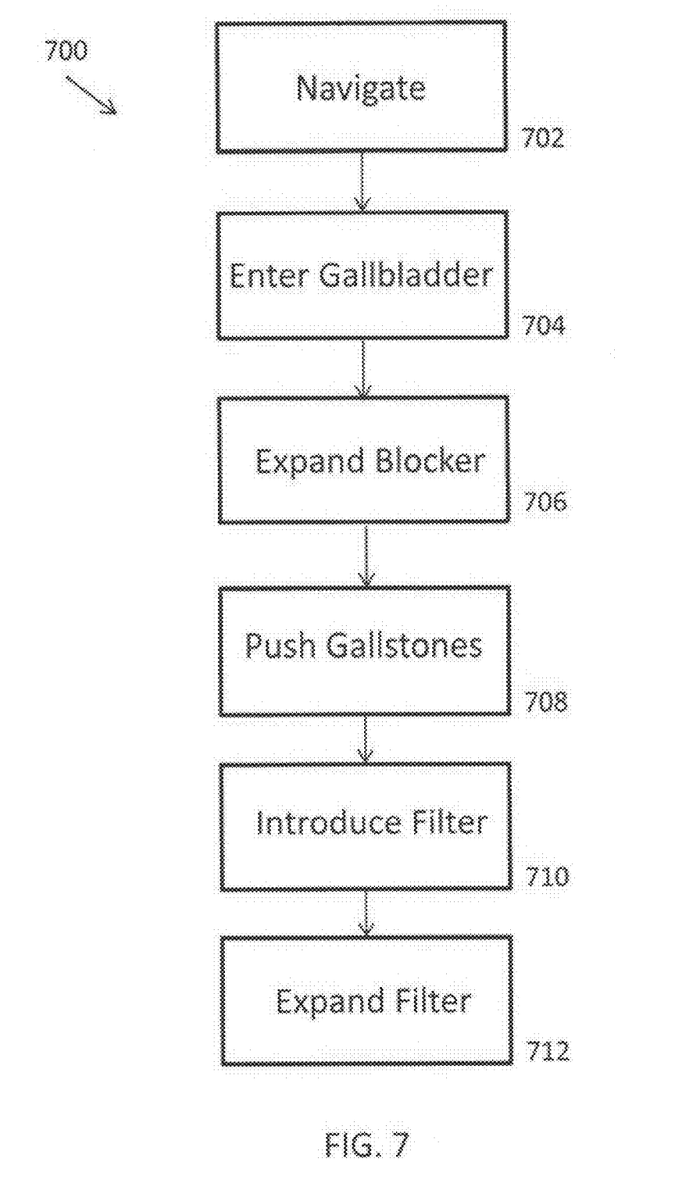
FIG. 7 is a flowchart of a method of deploying a filtering device in a gallbladder, in accordance with an exemplary embodiment of the invention.

FIG. 7 is a flowchart 700 depicting a method of implanting a filter device 200 in the gallbladder 104, in accordance with an embodiment of the invention. In an embodiment of the invention, implantation may be performed without general anesthesia and is considered to be minimally invasive. In an embodiment of the invention, the filter device 200 and/or the blocking device 100 are inserted and/or navigated (702) into the GI tract via the mouth, through to the esophagus, through to the stomach and then into the duodenum. Navigation and/or insertion are accomplished using an endoscope and/or a flexible guide wire/guiding rod and/or an elongated tool, such as a catheter 106, as chosen by the attending medical professional performing the procedure, in an embodiment of the invention.

The filter device 200 is advanced the Sphincter of Oddi/papila into the common bile duct, in an exemplary embodiment of the invention. A sphincterotomy of the Sphincter of Oddi is performed, if required and/or desired, similarly to the method commonly used in endoscopy and ERCP. The filter device 200 is implanted at a desired implantation site by navigating the filter device 200 from the common bile duct through to the cystic duct and/or the gallbladder 104. Contrast material in used order to image the gallbladder 104 and/or the cystic duct and/or the gastro-intestinal tract, in some exemplary embodiments of the invention. Optionally, other commonly available imaging techniques are used for the implantation, for example X-ray and/or ultrasound.

In an exemplary embodiment of the invention, the filter device 200 and/or the blocking device 100 are inserted and/or navigated (702) into the patient in a contracted form. In some embodiments of the invention, the blocking device 100 precedes the filter device 200 such that during implanting, the blocking device 100 enters (704) the gallbladder 104 first (shown in FIGS. 1A-1B), radially expands (706) in the gallbladder 104 (shown in FIGS. 1C-1D) and pushes (708) any gallstones 102 in the gallbladder 104 down to or at least towards a distal end of the gallbladder 104 and away from the gallbladder opening (shown in FIGS. 1D-1E), thereby clearing a space within the gallbladder for proper and/or full expansion of the filter device.

Figures 1A, 1B, 1C:
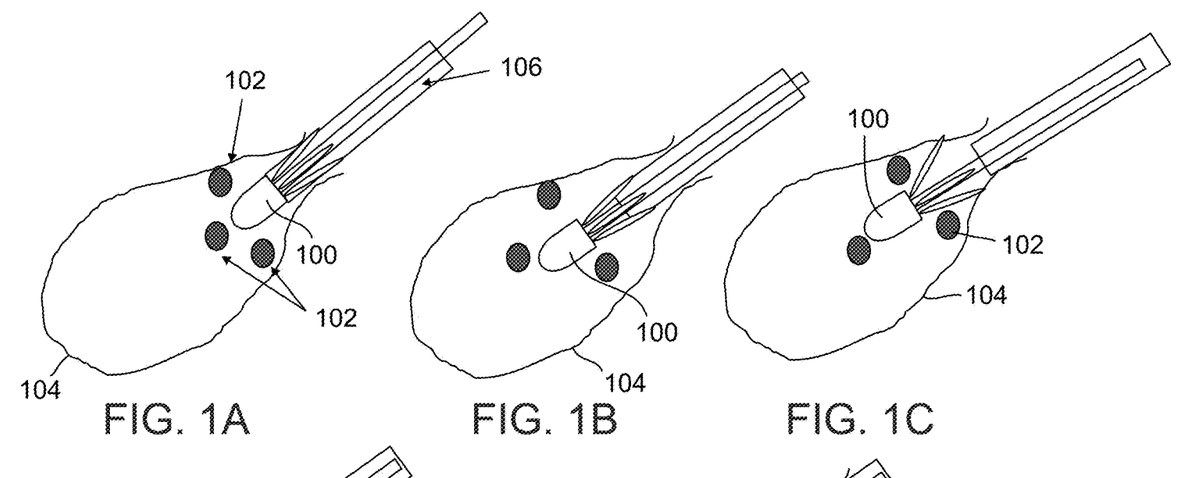
FIGS. 1A-1E are side views of a schematic deployment sequence of a blocking device, in accordance with an exemplary embodiment of the invention.
Figure 1D:
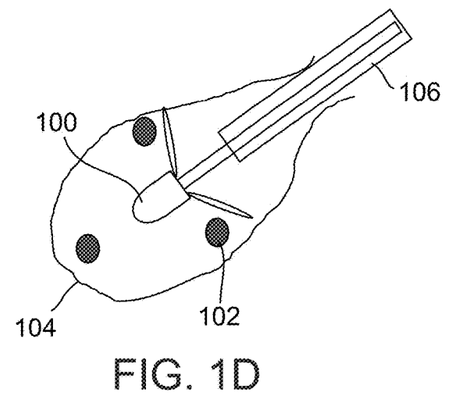
Figure 1E:
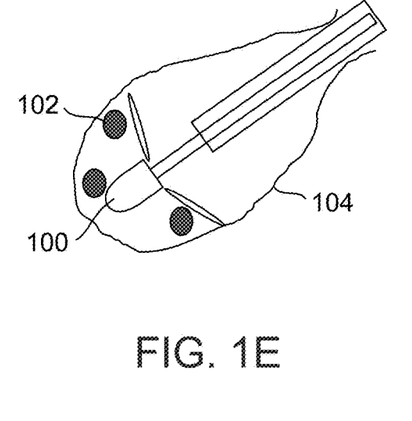
Figures 2A, 2B, 2C:
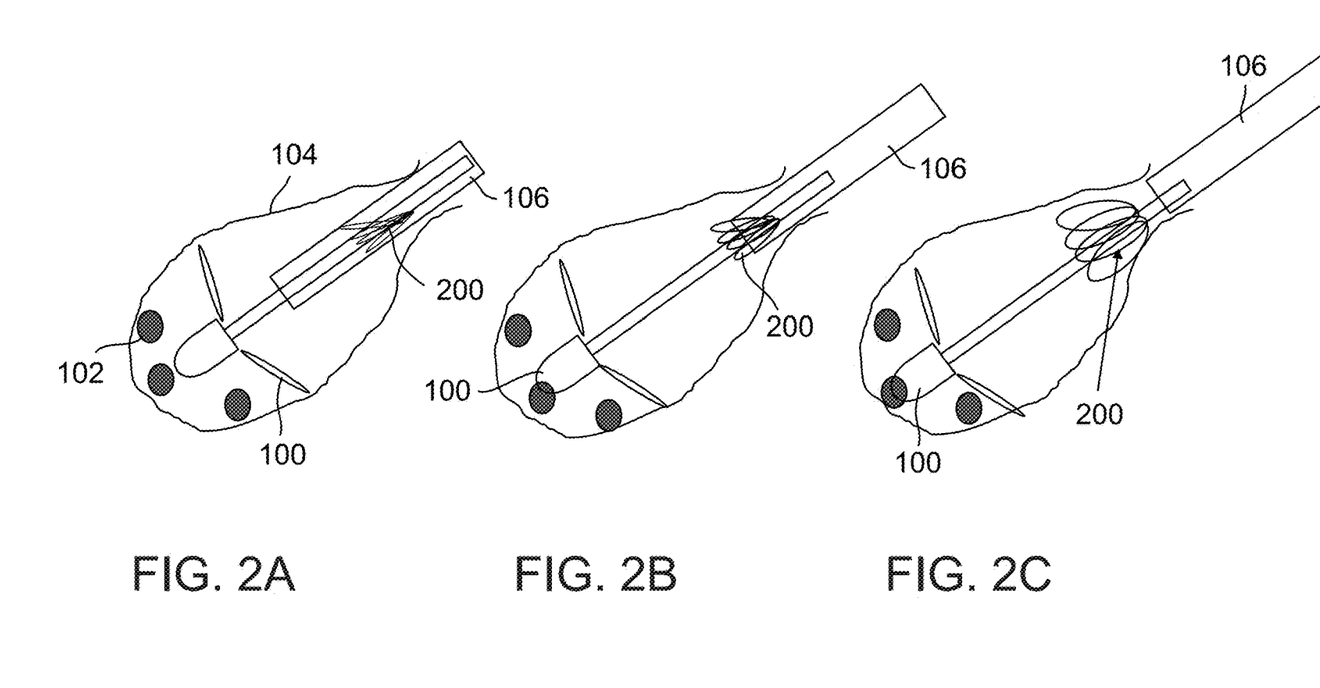
FIGS. 2A-2C are side views of a schematic deployment sequence of a filtering device after the blocking sequence shown in FIGS. 1A-1E has been performed, in accordance with an exemplary embodiment of the invention.

In an embodiment of the invention, the filter device 200 is then introduced (710) to the gallbladder 104 (now that the area in the gallbladder 104 near the opening has been cleared or substantially cleared of gallstones 102) so that the filter device 200 can properly expand (712) to provide filtering. Introduction of the filter device 200 and expansion in a cleared area is schematically shown in FIGS. 2A-2C. In some embodiments of the invention, the filter device 200 expands (712) to its intended size and shape upon arrival at the desired site of implantation.

In some embodiments of the invention, the filter device 200 is also provided with blocking capability and functionally operates to both block (to clear out gall stones to make room for filter expansion) and filter. Exemplary devices for performing both functions in the same device are shown and described with respect to FIGS. 3A-3C and FIGS. 4A-4C, below. In some embodiments of the invention, the blocking device 100 also functions as a filter, in addition to and/or alternatively to the filtering device 200.

In some embodiments of the invention, the filter device 200 expands (712) as a consequence of its own spring-like behavior, for example upon deployment from a catheter 106 which was used to pass the filter device 200 to the cystic duct and/or gallbladder 104, the device 200 springs into designed shape and size once the catheter 106 is no longer holding the filter device 200 in a contracted state. Optionally, the filter device 200 expands (712) as a result of its shape memory characteristic. In some embodiments of the invention, an expansion balloon is used to expand the filter device 200. Due to the special anatomic structure of the cystic duct in the gallbladder region, more than one balloon and/or one balloon inflation may be used, for example, using a flexible balloon for initial inflation and a rigid and/or a semi-rigid balloon for filter device fixation.

Optionally, the blocking device 100 is withdrawn after the filter device 200 has been deployed, for example through an opening in the filter device configured for passage of the blocking device 100 therethrough. Optionally, the opening is elastic, sphincter-like, and/or at least partially closes after the blocking device 100 passes through while being withdrawn.

Besides the implantation method described above, any other technique leading to the Sphincter of Oddi and/or the gallbladder 104, such as laparoscopy or open surgery, may be used.

In an embodiment of the invention, the filter device 200 and/or the blocking device 100 can be removed or are designed to be bio-absorbed at any time.

In some embodiments of the invention, medical imaging is used for guiding the navigation of the biliary tree and/or implantation of the blocking device 100 and/or filter device 200 at the correct implantation site. Optionally, a scope is used to provide imaging. Optionally, x-ray is used to provide imaging. Optionally, ultrasound is used to provide imaging.

Figures 3A, 3B, 3C:
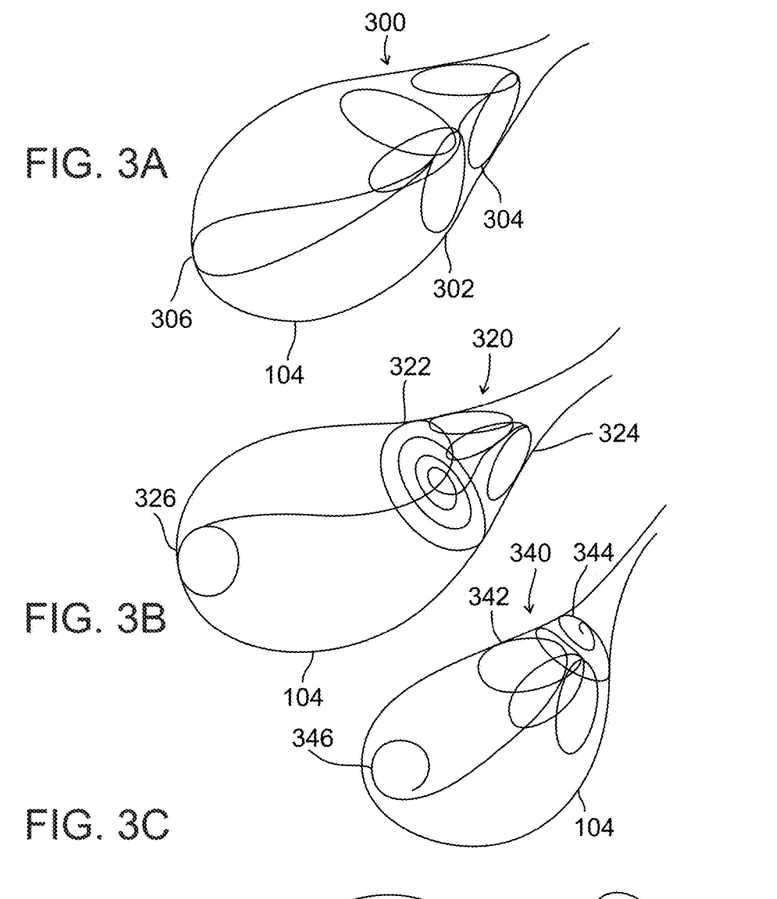
FIGS. 3A-3C are side views of two tier filtering devices, in accordance with exemplary embodiments of the invention.

FIGS. 3A-3C are side views of two tier filtering devices 300, 320, 340, respectively, in accordance with exemplary embodiments of the invention. In an embodiment of the invention, the two tier filtering devices 300, 320, 340 are provided with a combination filter/blocker portion 302, 322, 342, respectively and an anchoring portion 304, 324, 344, respectively.

In an embodiment of the invention, the filter/blocker portion 302, 322, 342 is configured to enter the gallbladder 104 prior to the second tier, or anchoring portion 304, 324, 344, which when the filter/blocker portion 302, 322, 342 expands pushes any gallstones away from the opening of the gallbladder 104, both to prevent gall stones from entering the biliary tree and also to ensure proper deployment/expansion of the anchoring portion 304, 324, 344.

In an embodiment of the invention, the anchoring portion does not exert radial force on the wall of the gallbladder 104 and/or does not anchor by attaching itself or latching onto a wall of the gallbladder 104. In some embodiments of the invention, the anchor portion 304, 324, 344 works in combination with a stopper 306, 326, 346 which when taken together stretch substantially the length of the gallbladder 104, preventing the devices 302, 320, 340 from moving axially in the gallbladder (that is, preventing the device from migrating away from the opening to gallbladder).

Figure 4A:
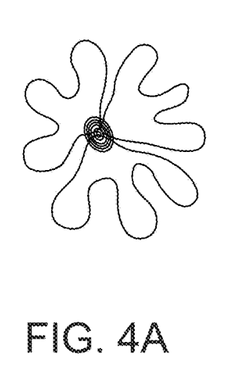
FIGS. 4A-4C are top views of the filtering portion of filtering devices, in accordance with exemplary embodiments of the invention.
Figure 4B:
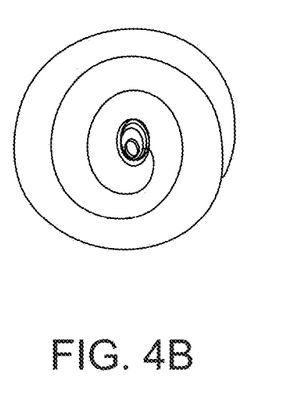
Figure 4C:
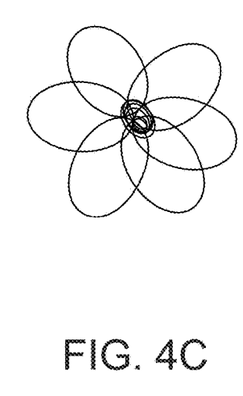

FIGS. 4A-4C are top views of the filter/blocking portions 302, 322, 342 of filtering devices 300, 320, 340, in accordance with exemplary embodiments of the invention. In some embodiments of the invention, at least the filter/blocking portion 302, 322, 342 is configured so that there is spacing between the wires sufficient for blocking gallstones of a specified minimum size, but are also far enough apart to avoid growth of bacterial films, and other bio-film growth, between the wires which could block the natural flow of material from the gallbladder into the biliary tree.

In some embodiments of the invention, the filter/blocking portion is configured to block gallstones approximately 5 mm or more in diameter. In some embodiments of the invention, spaces between wires form an opening no greater than 4 mm×4 mm.

In some embodiments of the invention, the filter portion and/or blocking portion and/or anchoring portion are mesh, spiral/coiled and/or a perforated sheet. In some embodiments of the invention, the device is shaped to allow for slight movement within the implantation site in order to prevent or delay bio-film growth via device motion. Optionally, the device is moved by movement of the gallbladder and/or the surroundings of the implantation site itself. In an embodiment of the invention, the device moves and/or flexes to cause any accumulation of bio-film to break, crack and/or at the very least create openings through the bio-film such that natural secretions of the gallbladder continue to flow.

The device material is selected to be biocompatible and/or bio-absorbable, in an exemplary embodiment of the invention. Optionally, the device is constructed of a polymer material. In some embodiments of the invention, the device is at least partly metal. Optionally, the device is at least a shape memory alloy such as nickel titanium, also known as Nitinol®. In some embodiments of the invention, at least a portion of the device is coated, for example with Teflon® or other similarly inert or highly non-reactive coating. Optionally, at least a portion of the device and/or the coating is adapted to elute a substance, for example a pharmaceutical. Optionally, an anti-bio-film agent, like an antibiotic, is eluted from and/or covers at least a portion of the device.

In some embodiments of the invention, the entire device is constructed of a single filament. In an embodiment of the invention, the blocking portion (if separate, such as in the case of the device shown in FIGS. 1A-1E) and/or the filter portion and/or anchoring portion are separately formed elements which are connected together. In some embodiments of the invention, at least two of the portions are connected by at least a single filament. Optionally, at least two of the sections are connected by a plurality of filaments.

Optionally, the anchoring portion 304, 324, 344 could have a configuration shown in any of FIGS. 4A-4C. Optionally, a separate blocking or filter portion could have a configuration shown in any of FIGS. 4A-4C.

Figure 5A:
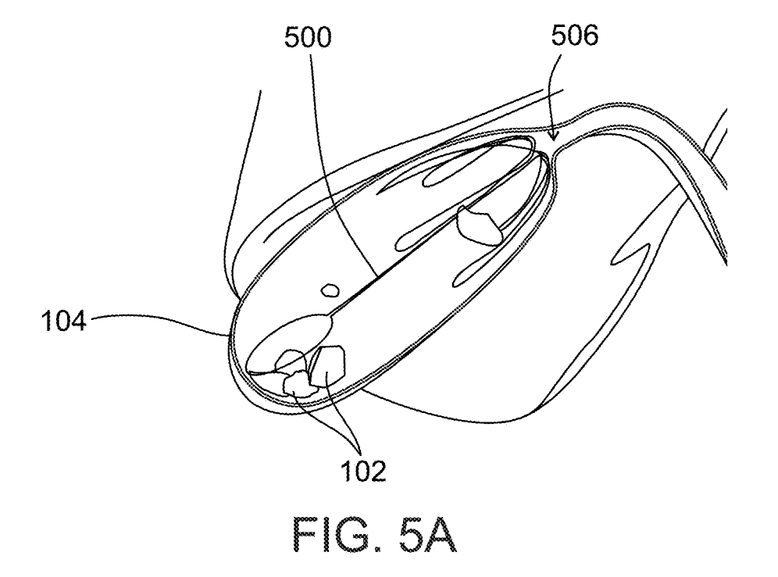
FIGS. 5A and 5B are perspective views of a filtering device, in accordance with an exemplary embodiment of the invention.
Figure 5B:
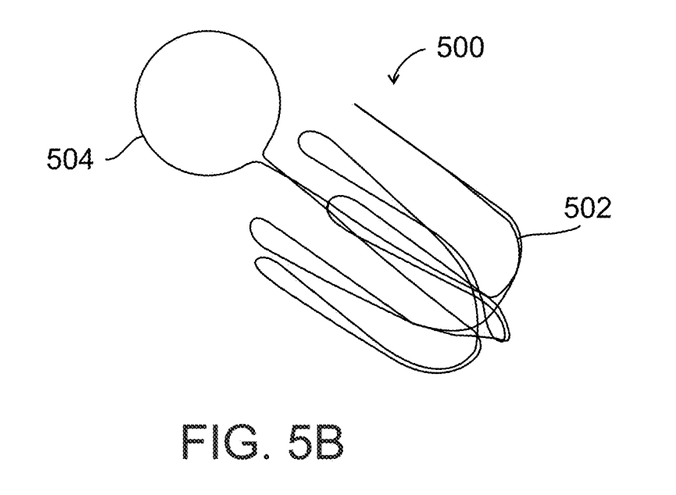

FIGS. 5A and 5B are perspective views of a filtering device 500, in accordance with an exemplary embodiment of the invention. FIG. 5B shows an exemplary filtering device 500 configured with a filter/blocking portion 502 and a stopper 504. FIG. 5A is a perspective view of a cross-sectioned gallbladder 104 with the filtering device 500 implanted within the gallbladder 104. In an embodiment of the invention, filtering device 500 is deployed after a blocking device 100 has been deployed. Optionally, the blocking device 100 is removed after the filtering device 500 has been placed in the gallbladder 104. In some embodiments of the invention, the filter/blocking portion 502 is located near an opening 506 to the gallbladder 104 to prevent gallstones 102 of a certain minimum size from leaving the gallbladder 104. In some embodiments of the invention, the stopper 504 is configured to avoid puncturing a wall of the gallbladder, for example by having a rounded shape. In some embodiments of the invention, the stopper 504 (including the length of filament leading to the stopper) and the filter/blocking portion 502 operate in conjunction (by substantially stretching the length of the gallbladder) to reduce the chance of movement of the filter/blocking portion 502 from migrating away from the opening 506.

Figure 5C:
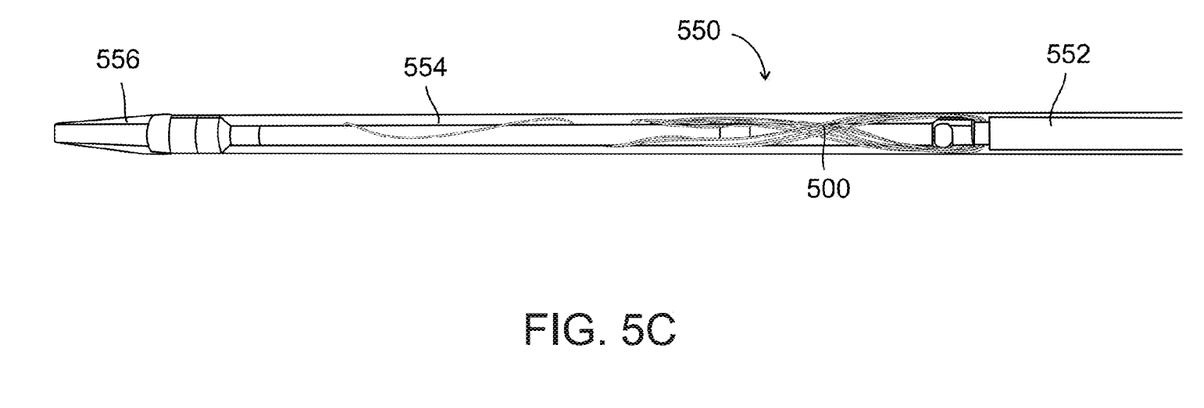
FIG. 5C is a side view of a filtering device delivery system, in accordance with an exemplary embodiment of the invention.
Figure 5D:
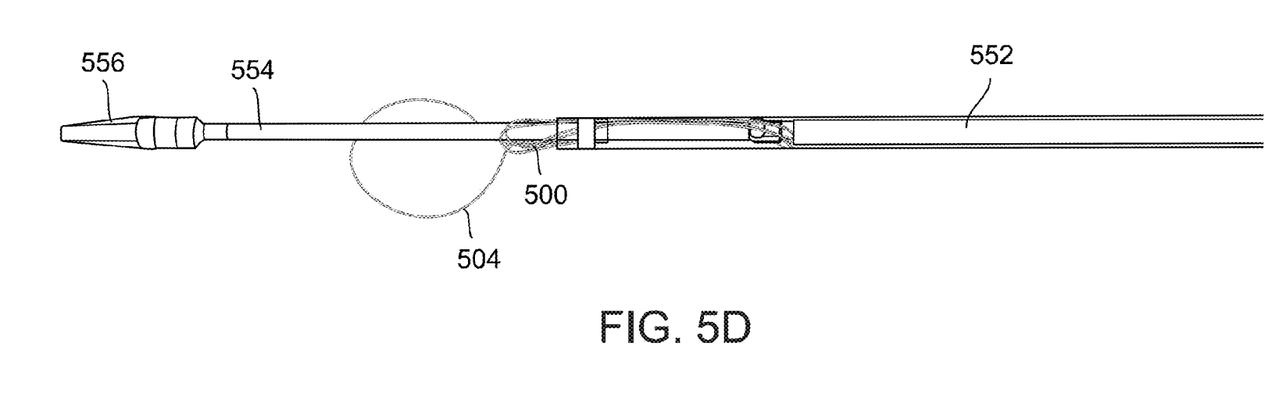
FIG. 5D is a side view of a filtering device delivery system with the filtering device partially deployed, in accordance with an exemplary embodiment of the invention.
Figure 8:
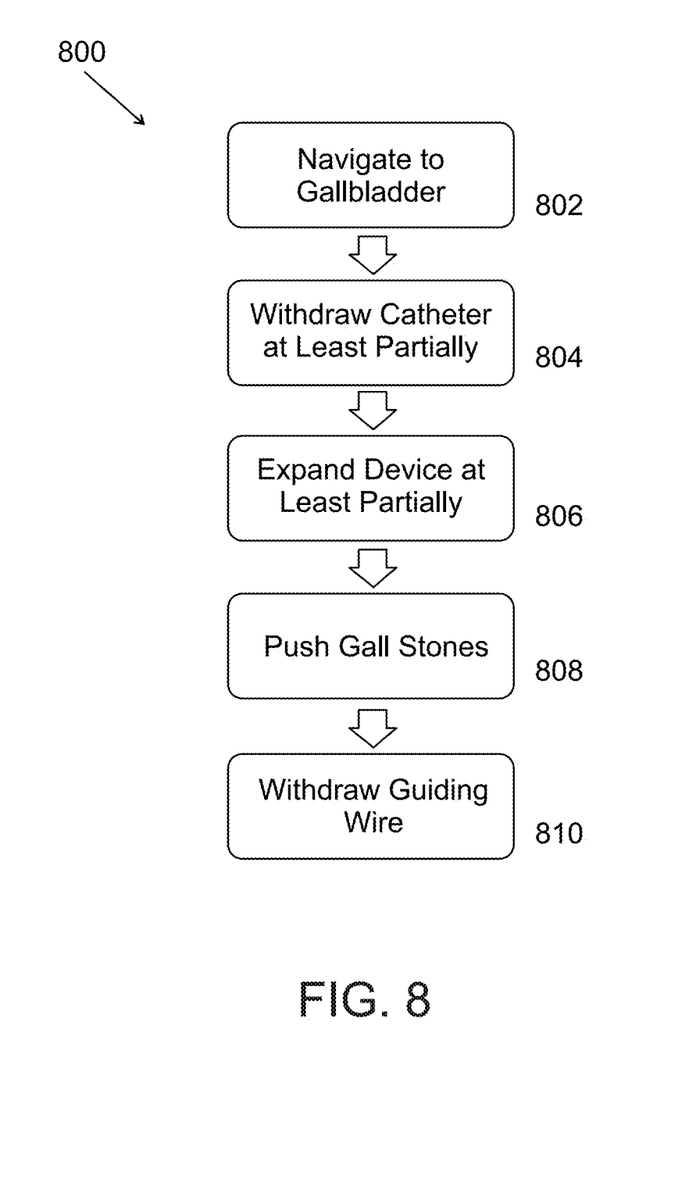
FIG. 8 is a flowchart of a method of deploying a filtering device in a gallbladder, in accordance with an exemplary embodiment of the invention.

FIG. 5C is a side view of a filtering device delivery system 550 for implanting a filtering device, for example filtering device 500, in accordance with an exemplary embodiment of the invention. For efficiency, the filtering device delivery system 550 of FIGS. 5C and 5D is described in conjunction with the a method of deploying a filtering device in a gallbladder shown in the flowchart 800 of FIG. 8. It should be understood, that while filtering device 500 is shown in FIGS. 5C and 5D, any of the filtering devices or filtering device variations described herein could be used and/or deployed as described herein. In an embodiment of the invention, a conventional delivery system for a biliary stent is used for delivery of a filtering device 500 (or any of the filtering devices described herein).

In an embodiment of the invention, the delivery system includes a catheter 552, within which a guiding rod 554 with a tip 556 mounted on a distal end of the guiding rod 554 is inserted. In some embodiments of the invention, the tip 556 is used for assisting with the navigation (802) of the catheter 552 within the patient to an implantation site, for example in the gallbladder. Optionally, the tip is configured to assist with the blocking of stones within the gallbladder during filter device 500 deployment, for example with reversibly deployable structures. In an embodiment of the invention, filtering device 500 is wrapped around guiding rod 554, between the guiding rod 554 and the catheter 552 (so the body of the patient is shielded from the filtering device). In some embodiments of the invention, filtering device 500 is placed substantially on one side of the guiding rod 554 (and temporarily trapped there by the catheter 552), such that deployment of the filtering device 500 is from the side when the catheter 552 is retracted instead of longitudinally axially. A substantially side-mounted filtering device 500 is shown in FIG. 5D, described in more detail below. It should be understood that side-mounting the filtering device 500 enables the retention of the guiding rod 554 in the implantation site while still allowing the device 500 to deploy. As described elsewhere, retention of the guiding rod 554 at least facilitates locating the device 500 within the implantation site or facilitates pushing stones distally in the gallbladder for unimpeded device 500 deployment, in an embodiment of the invention.

FIG. 5D is a side view of the filtering device delivery system 550 with the filtering device 500 partially deployed, in accordance with an exemplary embodiment of the invention. In an embodiment of the invention, the catheter 552 has been withdrawn (804) partially in a proximal direction, leaving the guiding rod 554, around which the filtering device 500 is wrapped, proximal to the implantation site. As the catheter 552 is withdrawn further, more and more of the filtering device 500 is deployed into the implantation site and at least partially expands (806) into shape. For example, the stopper 504 of filtering device 500 has assumed a loop configuration having been freed from the catheter 552, whereas it was compressed for delivery when it was within the catheter 552 and wrapped around the guiding rod 554. In some embodiments of the invention, the deployed stopper 504 (or other stoppers 1000, 1010, 1020 described herein) pushes (808) gall stones down in the gallbladder towards the distal wall of the gallbladder in order to provide sufficient space within the gallbladder near the gallbladder opening for unimpeded expansion of the filtering portion of the device 500. In an embodiment of the invention, the filtering device 500 when fully expanded and deployed will resemble the filtering device 500 depicted in FIG. 5B. In an embodiment of the invention, the guiding rod 554 is also withdrawn (810) from the implantation site, once the filtering device 500 has been fully deployed, leaving the filtering device 500 by itself within the implantation site, or gallbladder.

In some embodiments, pushing (808) is achieved by holding the catheter 552 in relative place while the filter device 500 is deployed stopper first and/or the guiding rod 554 is advanced distally. In some embodiments of the invention, the blocking portion/pusher are a part of the filter device, such as described herein, and/or are a part of the delivery system (e.g. the catheter or guiding rod). In some embodiments if the invention, the guiding rod 554 is used to assist with locating the filter device within the gallbladder or implantation site, for example where the filter device is wrapped around the guiding rod prior to deployment the guiding rod can located the filter device at a particular depth of insertion, or even direction of insertion, within the gall bladder. In some embodiments of the invention, the guiding rod is used for pushing (808) gall stones distally in the gallbladder prior to or during deployment of the filter device.

Figure 6:
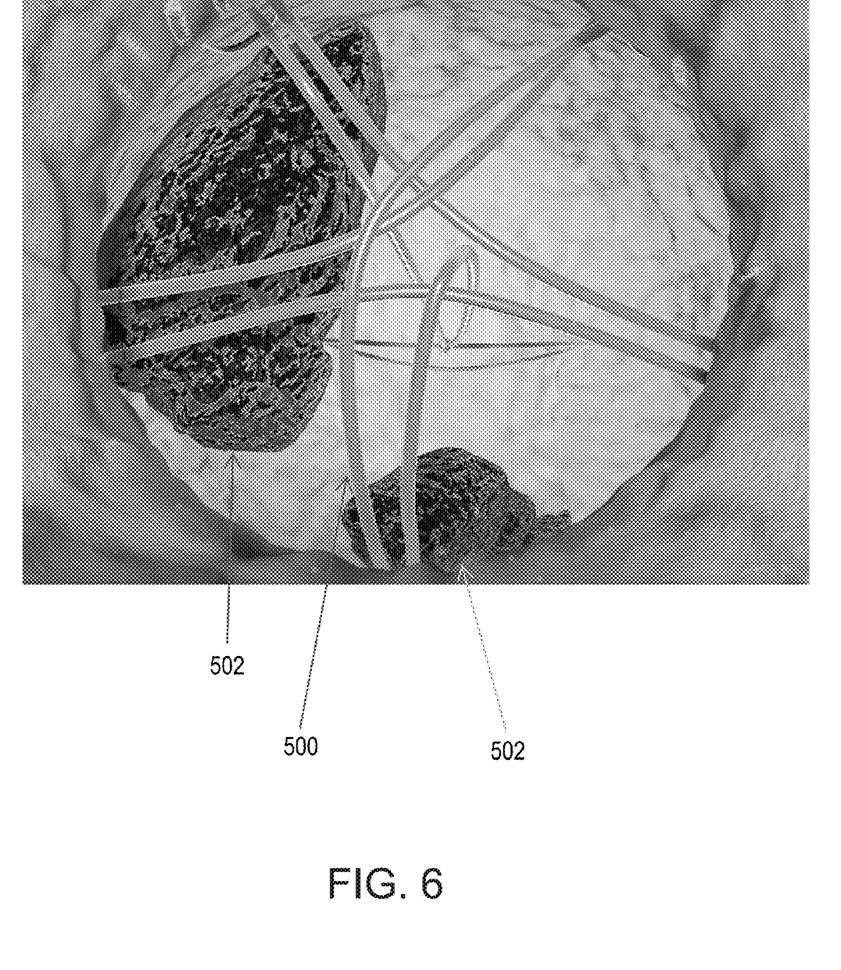
FIG. 6 is a top view of a filtering device in situ, in accordance with an exemplary embodiment of the invention.

FIG. 6 is a top view of a filtering device 600 in situ, in accordance with an exemplary embodiment of the invention. In an embodiment of the invention, the device 600 is blocking/filtering gall stones 602 of a specified minimum size and preventing them from leaving the gallbladder.

Figure 9A:
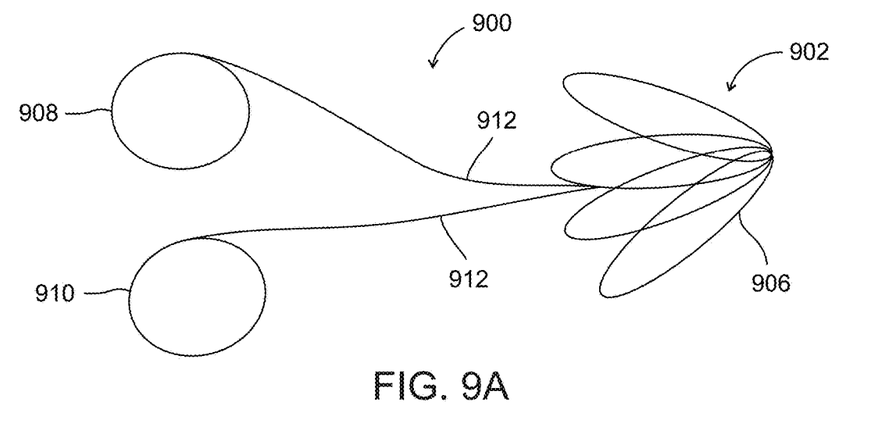
FIG. 9A is a side view of a filtering device with dense leaves and a split stopper, in accordance with an exemplary embodiment of the invention.

FIG. 9A is a side view of a filtering device 900 with leaves 906 of a filtering portion 902 and a split stopper 904, where the filtering portion 902 and the stopper 904 are connected by a tail 912, in accordance with an exemplary embodiment of the invention. In an embodiment of the invention, the leaves 906 are formed of the single wire of the device by repeated curves which give a leaf-like, but open, shape. In some embodiments of the invention, there are a plurality of formed leaves, for example anywhere from 2-7 leaves. Optionally, there are more leaves. In an embodiment of the invention, the number of leaves, which optionally overlap at least partially helps to determine the size of particles that are filtered by the filtering portion, wherein as the number of leaves increase, optionally overlapping, impede smaller and smaller stones are filtered. In some embodiments of the invention, the number of leaves helps to determine the amount of pressure exerted by the filter device on the surrounding body tissue, where generally the more leaves there are, the less pressure exerted on the body by any single one. In an embodiment of the invention, the leaves 906 are ovoid, spherical, circular or oblong shaped, as examples. In some embodiments of the invention, the tail 912, or a portion of it, is welded to at least one of the leaves 906. In some embodiments of the invention, any loose ends of the wire are attached, optionally by welding, such that there are no loose ends in a finished filtering device.

In some embodiments of the invention, the filtering device 900 has two stopper structures 908, 910 instead of one, such as shown in FIG. 5B. In an embodiment of the invention, the two stopper 908, 910 stopper configuration increases the contact area (over having just one stopper) between the filtering device 900 and a distal wall of the gallbladder and/or reduce pressure exerted on the stopper, generally, and subsequently the amount of counter-force applied by the device 900 on the gallbladder. In some embodiments of the invention, the filtering portion 902, the tail 912 and the stopper 904 are disposed entirely within the gallbladder, substantially uncompressed or shaped by the walls of the gallbladder, when implanted. In some embodiments of the invention, at least the two stopper structures 908, 910 and the tail 912 are all co-planar. In some embodiments of the invention, having at least two tails enables the filtering device 900 to adapt better to the size and/or shape of the gallbladder relative to a filtering device with only one tail, at least because the plurality of tails are more articulate. In an embodiment of the invention, the split tail/stopper configuration provides a deformation ability, optionally elastic deformation, to the filter device, for example upon the exertion of axial pressure on the device. Optionally, the stopper and/or tail represent 10%-40% of the device's overall length.

In some embodiments of the invention, the tails are of different lengths, for example to bias the filtering device in the gallbladder and/or to adapt the filtering device to a shape of the gallbladder. In some embodiments of the invention, having a plurality of stoppers provides redundancy in case at least one stopper is blocked from reaching the distal wall of the gallbladder by debris (e.g. stones) within the gallbladder.

Figure 9B:
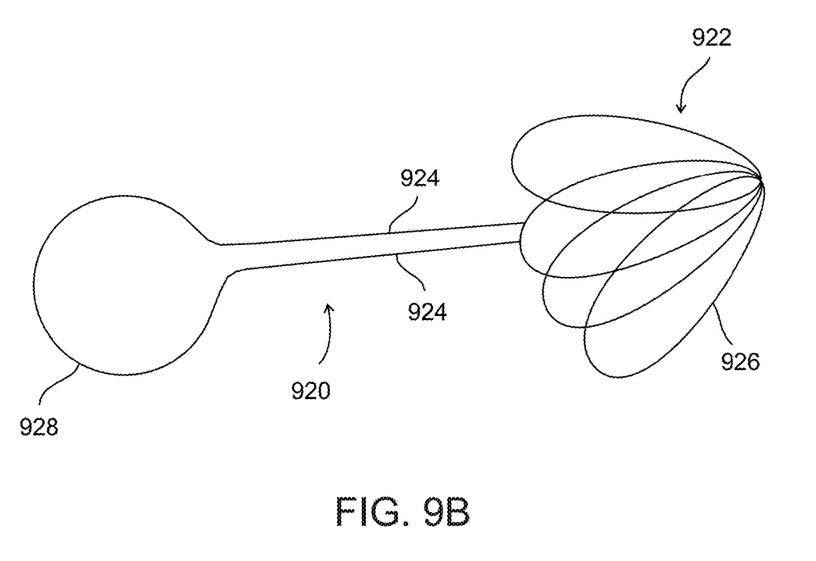
FIG. 9B is a side view of a filtering device with large overlapping leaves, in accordance with an exemplary embodiment of the invention.

FIG. 9B is a side view of a filtering device 920 with large overlapping leaves 926 of a filtering portion 922, in accordance with an exemplary embodiment of the invention. In an embodiment of the invention, the leaves 926 are configured to have a wider minor axis, in relation to other embodiments described herein, for example device 900. In an embodiment of the invention, the leaves 926 are ovoid or oblong shaped. In an embodiment of the invention, the tail/stopper are a variant of a leaf or petal, for example of generally similar shape to the leaves 926 but elongated.

In some embodiments of the invention, a leaf 926 occupies 30° to 120° in radial circumference around the longitudinal axis of the filter device, is between 1 cm and 10 cm in length and/or between 20% and 60% of a nominal gallbladder's length and/or up to 80% of a nominal gallbladder's maximal diameter. These ranges are given as guidelines only, and actual filter devices could be larger or smaller in any of the recited dimensions.

In an embodiment of the invention, the leaves 926 are configured to overlap in order to provide a filtering structure that will filter small diameter particulates, such as gallstones. It should be understood that as the amount of leaf overlapping is increased, the smaller the stones that will be filtered, in an embodiment of the invention.

In an embodiment of the invention, a stopper 928 of the device 920 is curved to minimize trauma to the patient and is connected to the filtering portion 922 by a tail 924.

In some embodiments of the invention, the filtering portion 922, the tail 924 and the stopper 928 are disposed entirely within the gallbladder, substantially uncompressed or shaped by the walls of the gallbladder, when implanted.

Figure 10A:
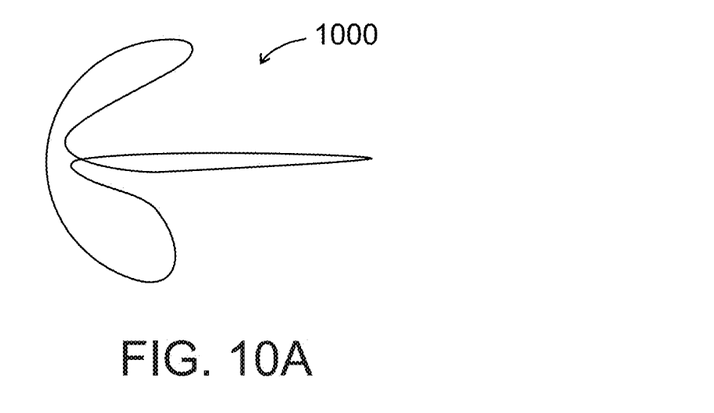
FIGS. 10A-10C are side views of different stopper configurations, in accordance with exemplary embodiments of the invention.
Figure 10B:
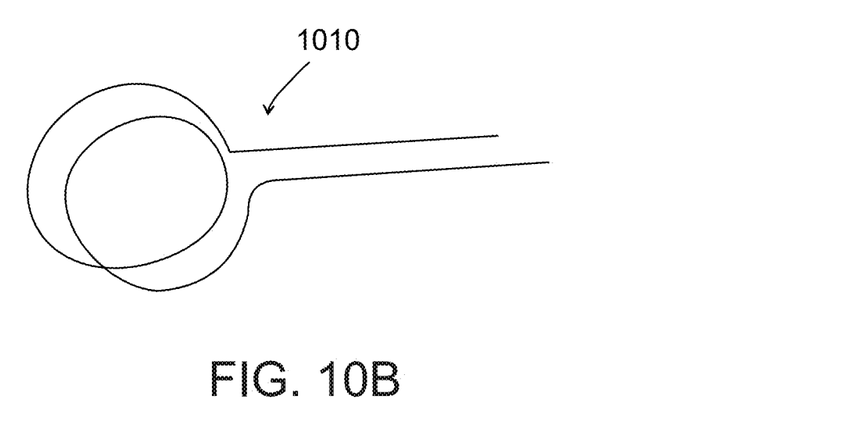
Figure 10C:
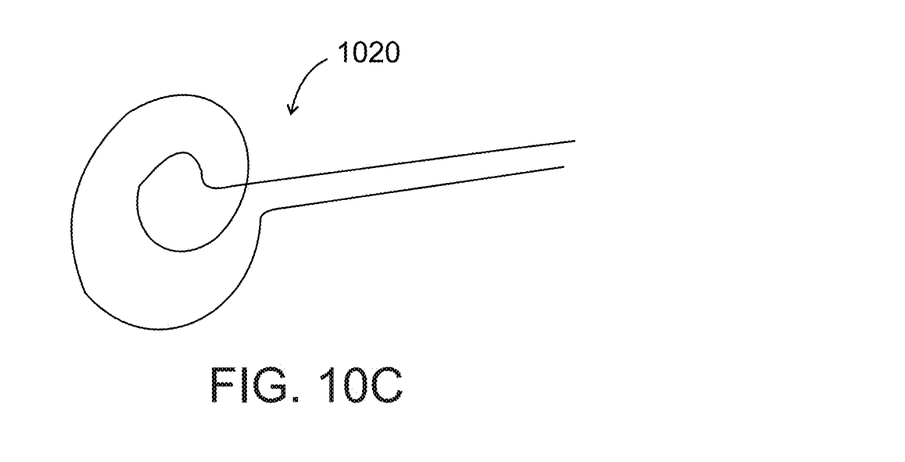

FIGS. 10A-10C are side views of different stopper configurations, in accordance with exemplary embodiments of the invention. It should be understood that the stopper configurations described with respect to FIGS. 10A-10C could be used with any of the filter devices described herein. It should also be understood that in some embodiments of the invention, the stopper portion (for example, those described in FIGS. 10A-10C) of a filtering device is usable in a similar fashion to the blocking device 100 or portions 302, 322, 342 described elsewhere herein, that is, to push gallstones to the distal portion of the gallbladder prior to deployment and expansion of the filtering section at least to allow for unimpeded expansion of the filtering section. In some embodiments of the invention, the stopper and/or the tail is configured to deform to provide compliance with various gallbladder sizes and/or geometries. Optionally, the stopper and/or tail designs are also configured to deform in order to maintain or decrease force applied to the gallbladder wall.

In some embodiments of the invention, the stoppers deploy in either two dimensions or three dimensions. Optionally, three-dimensional stoppers provide more prevention of filter device movement, more pressure reduction against the gallbladder wall and/or more compliance to gallbladder shape and/or exerted forces during use.

In an embodiment of the invention, FIG. 10A shows a stopper 1000 with a mushroom-like configuration (biased towards the opening of the gallbladder) intended to increase the surface area of contact between the filtering device and the wall of the gallbladder, thus decreasing the pressure exerted by area of the device on the patient.

FIG. 10B shows a stopper 1010 configured with a spring-like shape which could optionally be resilient, absorbing force to dampen pressure exerted on the wall of the gallbladder in which the filtering device is deployed.

FIG. 10C shows a stopper 1020 which is configured with concentric circles. In an embodiment of the invention, the concentric circles extend in three dimensions, for example extending perpendicular to the tail, increasing the contact area between the stopper and the gallbladder wall.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Further, described ranges are intended to include numbers outside any range described within statistical error and/or inherent measurement equipment limitations.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method for implanting a filter device in a gallbladder, comprising:
   navigating a catheter including the filter device wrapped around a guiding rod through an opening to the gallbladder for implantation, the filter device including at least a filtering portion, a tail and a stopper which spans a cross-sectional space of the gallbladder;

withdrawing at least partially said catheter, through which the guiding rod and filter device are inserted, from the implantation site;

expanding the stopper of the filter device at least partially by withdrawing at least partially the catheter, then pushing gall stones towards a distal wall of the gallbladder opposite the opening using the stopper while advancing the filter device;

expanding the filtering portion by introducing the filtering portion into the gallbladder while continuing to withdraw the catheter, wherein upon expansion, the filtering portion is disposed proximal to the opening of the gallbladder and the stopper is disposed near the distal wall of the gallbladder opposite the opening; and withdrawing the guiding rod from the implantation site, leaving the expanded filter device entirely within the gallbladder and substantially uncompressed.

2. The method according to claim 1, wherein the expanding includes expanding the stopper prior to expanding of the filtering portion.

3. The method according to claim 1, where the pushing is performed by at least one of the guiding rod and the stopper.

4. The method according to claim 1, wherein the filter device is implanted such that an attachment between two loose ends of the filter device does not abut a wall of the gallbladder.

\* \* \* \* \*